(12) United States Patent
Fabrega et al.

(10) Patent No.: US 8,592,174 B2
(45) Date of Patent: Nov. 26, 2013

(54) PEPTIDASE SUBSTRATES

(75) Inventors: Olivier Fabrega, Newcastle upon Tyne (GB); Arthur James, Cumbria (GB); Sylvain Orenga, Neuville sur Ain (FR); John Perry, Newcastle Upon Tyne (GB); Vindhya Salwatura, Newcastle Upon Tyne (GB); Stephen Stanforth, Northumberland (GB)

(73) Assignee: bioMérieux, S.A., Marcy l'Etuile (FR)

( * ) Notice: Subject to any disclaimer, the term of this patent is extended or adjusted under 35 U.S.C. 154(b) by 0 days.

(21) Appl. No.: 13/386,760

(22) PCT Filed: Jul. 28, 2010

(86) PCT No.: PCT/FR2010/051597
§ 371 (c)(1),
(2), (4) Date: Jan. 24, 2012

(87) PCT Pub. No.: WO2011/012809
PCT Pub. Date: Feb. 3, 2011

(65) Prior Publication Data
US 2012/0122135 A1 May 17, 2012

(30) Foreign Application Priority Data
Jul. 30, 2009 (FR) ...................................... 09 03768

(51) Int. Cl.
*C12Q 1/37* (2006.01)
*C07D 231/00* (2006.01)
*A61K 38/06* (2006.01)

(52) U.S. Cl.
USPC ............................... 435/24; 530/331; 546/180

(58) Field of Classification Search
None
See application file for complete search history.

(56) References Cited

U.S. PATENT DOCUMENTS

| | | | |
|---|---|---|---|
| 6,046,016 | A | 4/2000 | Orenga |
| 6,649,365 | B1 | 11/2003 | Orenga |
| 2008/0293094 | A1 | 11/2008 | James et al. |
| 2010/0099128 | A1 | 4/2010 | Fabrega et al. |

FOREIGN PATENT DOCUMENTS

| | | |
|---|---|---|
| EP | 0375723 | 3/1994 |
| FR | 2916763 | 12/2008 |
| WO | WO 98/04735 | 2/1998 |
| WO | WO 99/38995 | 8/1999 |
| WO | WO 2006/030119 | 3/2006 |

OTHER PUBLICATIONS

English language the International Search Report dtd Feb. 9, 2011 for PCT/FR2010/051597.
English language the Written Opinion dtd Feb. 3, 2012 for PCT/FR2010/051597.
Manafi et al, Fluorogenic and Chromogenic Substrates used in Bacterial Diagnostics, Microb Review, 1991, pp. 335-348, vol. 55, No. 3.
Co-pending U.S. Appl. No. 13/386,578, titled "Novel Peptidase Substrates" filed Jan. 23, 2012.
Co-pending U.S. Appl. No. 13/386,750, titled "Novel Peptidase Substrates" filed Jan. 24, 2012.
Co-pending U.S. Appl. No. 13/387,295, titled "Novel Nitroreductase Enzymatic Substrates" filed Jan. 26, 2012.
Co-pending U.S. Appl. No. 13/387,636, titled "Novel Nitroreductase Enzymatic Substrates" filed Jan. 27, 2012.
Co-pending U.S. Appl. No. 13/387,280, titled "Novel Nitroreductase Enzymatic Substrates" filed Jan. 26, 2012.

*Primary Examiner* — Robert Mondesi
*Assistant Examiner* — Younus Meah

(57) ABSTRACT

The present invention relates to the use of a compound of the following formula (I), as an enzyme substrate for the detection of a peptidase activity or as a pH indicator:

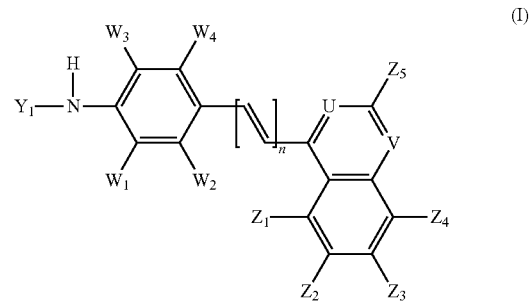

(I)

according to which:
  $Y_1$ is a peptide, H or an alkyl;
  $W_1$, $W_2$, $W_3$ and $W_4$ are independently H, Br, Cl, F, I, alkyl, alkoxy, thiomethyl, perfluoroalkyl, nitro, cyano, carboxyl (including the esters or amides thereof) or any combination thereof;
  n=0, 1 or 2;
  U is N or $N^+R$ and V is $CZ_6N$ or $N^+R$ or else V is N or $N^+R$ and U is $CZ_6$;
  R is H, alkyl, aralkyl, aryl, alkanoyl or alkylsulfonyl;
  $Z_1$, $Z_2$, $Z_3$, $Z_4$ and $Z_5$ are independently H, Br, Cl, F, I, alkyl, aryl, alkoxy, perfluoroalkyl, nitro, cyano, carboxyl, sulfonyl, including the carboxyl or sulfonyl esters or amides,
and salts thereof.

8 Claims, No Drawings

PEPTIDASE SUBSTRATES

CROSS REFERENCE TO RELATED APPLICATIONS

This application is the national stage application under 35 USC 371 of International Application No. PCT/FR2010/051597, filed Jul. 28, 2010, which claims priority to French Patent Application No. 0903768, filed Jul. 30, 2009, the disclosures of which are hereby incorporated by reference.

The present invention relates to novel compounds that can be used as pH indicators and/or as enzyme substrates for the detection of peptidase activity. These substrates can be used in applications comprising an enzymatic hydrolysis step producing a physicochemical signal, in particular in microbiology, biochemistry, immunology, molecular biology, histology, etc. The invention also relates to reaction media containing such substrates, the use of the substrates or of the media for the detection of peptidase activities and/or the differentiation of Gram-positive bacteria with respect to Gram-negative bacteria, and to methods of use.

A very large number of media for the detection of microorganisms currently exists. This detection may be based in particular on the use of particular substrates specific for an enzyme of the microorganism that it is desired to detect. Generally, synthetic substrates of enzymes are formed in such a way that the substrate and the product of its metabolism by the target enzyme have different physicochemical properties, making it possible to distinguish them and to evaluate whether all or part of the substrate has been converted to product by the enzyme. Hydrolase substrates generally consist of a first part specific for the enzymatic activity to be revealed and of a second part which acts as marker, which is generally chromogenic or fluorescent. Thus, in the case of bacteria, through the choice of substrates, depending on whether or not there is a reaction, it is possible to characterize the nature of a microorganism. A peptidase activity can in particular be used to reveal a group, a genus or a species of bacteria. Thus, alanine aminopeptidase activity, for example, makes it possible to differentiate Gram-negative bacteria from Gram-positive bacteria.

Enzymatic chromogenic substrates for the detection of peptidase activity are known from the prior art. Mention may be made in particular of the publication by Manafi (Manafi et al., Microbiol Rev 55(3): 335-348, 1991), which is a review of enzyme substrates used in microbiology. However, the aminopeptidase substrates described release, by hydrolysis, compounds which diffuse in the medium (beta-naphthylamine, 7-amino-4-methylcoumarin). As a result, in a heterogeneous reaction medium (colonies on Petri dishes, histological section, etc.), it is not possible to precisely localize the site of the hydrolysis. Mention may also be made of the substrates described in patent applications WO 98/04735 and WO 99/38995 filed by the applicant. However, although these substrates diffuse little in culture medium, they have certain drawbacks: they are difficult to synthesize, purity is low, yields are low and they are toxic with respect to certain microorganisms.

The present invention therefore proposes the use of novel compounds, either as pH indicators, or as peptidase substrates, which enable the detection of microorganisms. Compared with the existing substrates, these novel compounds are easy to synthesize, and can be used in particular in gelled media for the detection of microorganisms since they produce a coloration which diffuses little or not at all in the reaction medium. In the context of use as an enzyme substrate, this makes it possible to pinpoint a colony or an organelle expressing a peptidase activity among others which do not express it.

Before going any further with the description of the invention, the definitions below are given in order to facilitate the disclosure of the invention.

The term "enzyme substrate" is intended to mean a substrate that can be hydrolyzed by an enzyme into a product that allows the direct or indirect detection of a microorganism, of a cell or of an organelle. This substrate comprises in particular a first part that is specific for the enzymatic activity to be revealed and a second part that acts as a marker.

The compounds according to the invention that are used as substrates are suitable for use in flow cytometry because, since the product of the hydrolysis remains mainly localized in the cell expressing the enzymatic activity, it is possible to specifically count the cells expressing this activity, or even to separate them from the rest of the sample.

The compounds according to the invention that are used as substrates are also very suitable for use in histoenzymology, because, since the product of hydrolysis remains principally localized on the site of the hydrolysis, it is possible specifically to identify the cells or organelles expressing this activity within a tissue.

Owing to their low toxicity, the compounds according to the invention are very suitable, respectively, as pH indicators, or for monitoring peptidase activity in cell culture.

The compounds according to the invention are particularly suitable for use in a detection and/or identification medium since they produce a coloration or a fluorescence which does not diffuse in the reaction medium.

In the present application, the term "coloration" is used to cover a coloration, absorption of light in the visible spectrum, or a fluorescence, and absorption at one wavelength ($\lambda_{ex}$) and emission at a higher wavelength ($\lambda_{em}$, $\lambda_{em} > \lambda_{ex}$).

The compounds of the invention may be salified, i.e. in the form of a salt, such as chloride, bromide, iodide or trifluoroacetate.

The term "pH indicator" is intended to mean a chemical substance of which the color and/or the fluorescence vary(ies) according to the modifications in pH of the medium, said modifications being optionally linked to the metabolism of the microorganism(s) growing on said medium.

The term "peptidase" is intended to mean an enzyme capable of cleaving, by hydrolysis, the amide group formed between the acyl residue of a peptide and a primary amine. The term "aminopeptidase" is intended to mean an enzyme capable of cleaving, by hydrolysis, the amide group formed between an acyl of an amino acid and a primary amine. In the present application, the term "peptidase" can denote, as appropriate, both a peptidase and an aminopeptidase as defined above.

The term "peptide" is intended to mean a peptide chain comprising from 1 to 10 amino acids, preferentially from 1 to 4 amino acids. Preferentially, the peptide is a di-alanine or tri-alanine. The term "amino acid" is intended to mean any natural or unnatural amino acid known to those skilled in the art. According to one particular embodiment of the invention, the amino acid is a beta-alanine or L-alanine or D-alanine, or a glycine, pyrroglutamyl, etc.

Said peptide may comprise a blocking agent at its N terminal end. Blocking agents according to the invention comprise any blocking agent known to those skilled in the art which is capable of protecting amines. By way of example, mention may be made of t-butoxycarbonyl (N-tBOC), 9-fluorenyloxycarbonyl, a solubilizing agent such as succinyl, or else a non-metabolizable amino acid, i.e. an unnatural amino acid, such as pipecolic acid or the D form of an amino acid, such as D-phenylalanine. The blocking agents are not systematically present in the compounds of the invention.

The term "alkyl group" is intended to mean a chain of saturated hydrocarbon-based groups, such as, in particular, a $C_1$-$C_6$ alkyl, i.e. a straight or branched alkyl containing from 1 to 6 carbon atoms. By way of example, mention may be made of methyl, ethyl, propyl, isopropyl, butyl, t-butyl, pentyl, isopentyl and hexyl.

The term "aryl group" is intended to mean a functional group (or substituent) which derives from an aromatic nucleus such as, in particular, a $C_6$-$C_{10}$ aromatic nucleus, in particular phenyl, benzyl, 1-naphthyl or 2-naphthyl.

The term "carboxyl group" is intended to mean, in particular, a functional group composed of a carbon atom bonded via a double bond to a first oxygen atom, and via a single bond to a second oxygen atom, which is itself negatively charged or linked to a hydrogen atom. Depending on the $pK_a$ of the molecule and on the pH of the medium, the carboxyl group may be in ionized form, i.e. without H bonded to the second oxygen atom, which is then negatively charged.

The term "reaction medium" is intended to mean a medium comprising all the components required for the expression of a metabolism and/or for the growth of microorganisms, of a cell or of an organelle. This reaction medium can be used in flow cytometry, histoenzymology, cell culture, etc., or as a medium for detecting and/or identifying microorganisms.

The reaction medium may comprise one or more components in combination, such as amino acids, peptones, carbohydrates, nucleotides, minerals, vitamins, antibiotics, surfactants, buffers, phosphate salts, ammonium salts, sodium salts or metal salts.

The medium may also comprise a dye. By way of indication, mention may be made, as dye, of Evans blue, neutral red, sheep blood, horse blood, an opacifier such as titanium oxide, nitroaniline, malachite green, brilliant green, etc.

The reaction medium may be solid, semisolid or liquid. The term "solid medium" is intended to mean, for example, a gelled medium. Agar is the conventional gelling agent in microbiology for the culturing of microorganisms, but it is possible to use gelatin or agarose. A certain number of preparations are commercially available, for instance Columbia agar, Trypcase-soy agar, MacConkey agar, Sabouraud agar or, more generally, those described in the Handbook of Microbiological Media (CRC Press).

The reaction medium may be a detecting and/or identifying medium, i.e. a revealing medium or a culturing and revealing medium. In the first case the culturing of the microorganisms is carried out before inoculation and, in the second case, the detecting and/or identifying medium also constitutes the culture medium.

The term "biological sample" is intended to mean a clinical sample, derived from a specimen of biological fluid, or a food sample, derived from any type of food, or a cosmetic or pharmaceutical sample derived from any cosmetic or pharmaceutical preparation. This sample may thus be liquid or solid and mention may be made, in a nonlimiting manner, of a clinical sample of blood, plasma, urine, or feces, of nose, throat, skin, wound or cerebrospinal fluid specimens, a food sample from water, from drinks such as milk or a fruit juice; from yogurt, from meat, from eggs, from vegetables, from mayonnaise, from cheese; from fish, etc., a food sample derived from an animal feed, such as, in particular, a sample derived from animal meal. The sample may also be derived from a clinical environment specimen, a livestock specimen or a food, cosmetic or pharmaceutical production specimen. The term "environment specimen" is intended to mean in particular a surface, liquid, raw-material or product specimen. The term "sample" is therefore intended to mean both the specimen in itself (swab, stools, foods, etc.) and colonies of microorganisms resulting from said specimen (for example after isolation on a gelled culture medium, or in an enrichment broth inoculated with said specimen).

For the purpose of the present invention, the term "microorganism" covers bacteria, yeasts, molds, and more generally, organisms which in general are single-cell organisms, and invisible to the naked eye, and which can be multiplied or manipulated in the laboratory.

By way of Gram-negative bacteria, mention may be made of the bacteria of the following genera: *Pseudomonas, Escherichia, Salmonella, Shigella, Enterobacter, Klebsiella, Serratia, Proteus, Campylobacter, Haemophilus, Morganella, Vibrio, Yersinia, Acinetobacter, Branhamella, Neisseria, Burkholderia, Citrobacter, Hafnia, Edwardsiella, Aeromonas, Moraxella, Pasteurella, Providencia, Actinobacillus, Alcaligenes, Bordetella, Cedecea, Erwinia, Pantoea, Ralstonia, Stenotrophomonas, Xanthomonas* and *Legionella*.

By way of Gram-positive bacteria, mention may be made of the bacteria of the following genera: *Aerococcus, Enterococcus, Streptococcus, Staphylococcus, Bacillus, Lactobacillus, Listeria, Clostridium, Gardnerella, Kocuria, Lactococcus, Leuconostoc, Micrococcus, Falkamia, Gemella, Pediococcus, Mycobacterium* and *Corynebacterium*. By way of yeasts, mention may be made of the yeasts of the following genera: *Candida, Cryptococcus, Saccharomyces* and *Trichosporon*.

Preferentially, the microorganism is chosen from *Escherichia coli, Serratia marcescens, Enterobacter cloacae, Salmonella typhimurium, Providencia rettgeri, Yersinia enterocolitica, Pseudomonas aeruginosa, Bacillus subtilis, Listeria monocytogenes, Staphylococcus aureus, Streptococcus pyogenes* and *Enterococcus faecalis*.

In this respect, the invention relates to the use of a compound of the following formula (I), as an enzyme substrate for the detection of a peptidase activity and/or a variation in pH:

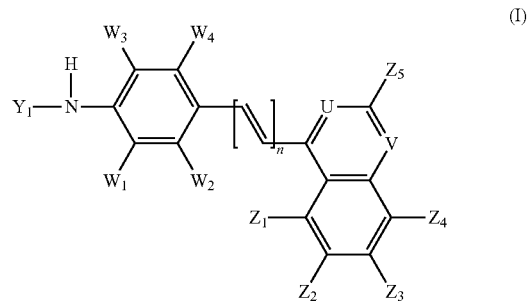

according to which:
- $Y_1$ is a peptide, H or an alkyl;
- $W_1$, $W_2$, $W_3$ and $W_4$ are independently H, Br, Cl, F, I, alkyl, alkoxy, thiomethyl, perfluoroalkyl, nitro, cyano, carboxyl (including the esters or amides thereof) or any combination thereof;
- n=0, 1 or 2;
- U is N or $N^+R$ and V is $CZ_6N$ or $N^+R$ or else V is N or $N^+R$ and U is $CZ_6$;
- R is H, alkyl, aralkyl, aryl, alkanoyl or alkylsulfonyl;
- $Z_1$, $Z_2$, $Z_3$, $Z_4$, $Z_5$ and $Z_6$ are independently H, Br, Cl, F, I, alkyl, aryl, alkoxy, perfluoroalkyl, nitro, cyano, carboxyl, sulfonyl, including the carboxyl or sulfonyl esters or amides, and salts thereof.

When said compound of formula (I) is used for detecting only a variation of pH, $Y_1$ is H or an alkyl.

When said compound of formula (I) is used for the detection of a peptidase activity, $Y_1$ is a peptide. Preferentially U or V is N.

When said compound of formula (I) is used for the detection of a peptidase activity and of a variation in pH, $Y_1$ is a peptide. Preferentially U or V is N.

According to one preferred embodiment of the invention, $Y_1$ is a peptide, preferentially chosen from among alanine, asparagine, glutamine, tyrosine and tri-alanyl.

According to one preferred embodiment of the invention, n=1.

According to one preferred embodiment of the invention, $W_1$, $W_2$, $W_3$ and $W_4$ are independently H.

According to one preferred embodiment of the invention, U is CH and V is N or $N^+R$, preferentially $N^+CH_3$.

According to one preferred embodiment of the invention, V is CH and U is N or $N^+R$, preferentially $N^+CH_3$.

According to one preferred embodiment of the invention, $Z_1$, $Z_2$, $Z_3$, $Z_4$, $Z_5$ and $Z_6$ are independently H.

According to one preferred embodiment of the invention, L-alanyl-4-(4'-amidophenyl)-2-methylquinoline, L-alanyl-4-(4'-amidostyryl)-N-benzylquinolinium TFA, L-glutamyl-4-(4'-amidostyryl)-N-benzylquinolinium TFA, beta-alanyl-4-(4'-amidostyryl)-N-benzylquinolinium TFA, L-alanyl-4-(4'-amidostyryl)-N-methylquinolinium TFA, D-alanine-N-methyl-4-(4'-aminostyryl)quinolinium (dichloride), L-alanyl-2-(4'-amidostyryl)-N-methylquinolinium, Z-alanyl-2-(4'-amidostyryl)-N-methylquinolinium, L-alanyl-4-(4'-amidostyryl)-N-methylquinolinium (dichloride), L-alanyl-L-alanyl-4-(4'-amidostyryl)-N-methylquinolinium (dichloride), L-alanyl-L-alanyl-L-alanyl-4-(4'-amidostyryl)-N-methylquinolinium (dichloride), γ-aminobutyryl-4-(4'-amidostyryl)-N-methylquinolinium di-Cl, L-asparaginyl-4-(4'-amidostyryl)-N-methylquinolinium-bis-TFA, -aspartyl-4-(4'-amidostyryl)-N-methylquinolinium dichloride, β-aspartyl-4-(4'-amidostyryl)-N-methylquinolinium dichloride, glycyl-4-(4'-amidostyryl)-N-methylquinolinium (dichloride), L-gamma-glutamyl-4-(4'-amidostyryl)-N-methylquinolinium (dichloride), glycyl-4-(4'-amidostyryl)-N-methylquinolinium chloride, L-leucyl-4-(4'-amidostyryl)-N-methylquinolinium dihydrochloride, L-methionyl-4-(4'-amidostyryl)-N-methylquinolinium di-Cl, pyroglutamyl-4-(4'-amidostyryl)-N-methylquinolinium iodide, sarcosinyl-4-(4'-amidostyryl)-N-methylquinolinium dichloride, L-tryptophanyl-4-(4-amidostyryl)-N-methylquinolinium dihydrochloride, L-tyrosyl-4-(4'-amidostyryl)-N-methylquinolinium dihydrochloride, beta-alanyl-2-(4'-amidostyryl)-N-methylquinolinium TFA, L-prolyl-2-(4'-amidostyryl)-N-methylquinolinium (HBr), Z-arginyl-2-(4'-amidostyryl)-N-methylquinolinium, L-pyroglutamyl-2-(4'-amidostyryl)-N-methylquinolinium, L-alanyl-4-(4'-amidostyryl)quinoline TFA, β-alanyl-4-(4'-amidostyryl)quinoline, L-glutamyl-4-(4'-amidostyryl)quinoline TFA, glycyl-4-(4'-amidostyryl)quinoline TFA, pyroglutamyl-4-(4'-amidostyryl)quinoline, L-alanyl-2-(4'-amidostyryl)quinoline, β-alanyl-2-(4'-amidostyryl)quinoline, glycyl-2-(4'-amidostyryl)quinoline TFA and L-alanyl-2-(2'-pyridyl)-4-(4"-amidostyryl)quinoline.

According to one preferred embodiment of the invention, said compound is chosen from: β-alanyl-2-(4'-amidostyryl)quinoline (β-Ala-ASQ), L-tyrosyl-4-(4'-amidostyryl)-N-methylquinolinium dihydrochloride (Tyr-ASQM$^+$), L-asparaginyl-4-(4'-amidostyryl)-N-methylquinolinium-bis-TFA (Asn-ASQM$^+$), L-gamma-glutamyl-4-(4'-amidostyryl)-N-methylquinolinium (dichloride) (λ-Glu-ASQM$^+$), and L-alanyl-L-alanyl-L-alanyl-4-(4'-amidostyryl)-N-methylquinolinium (dichloride) (Tri-Ala-ASQM$^+$).

The invention also relates to a method for the detection in microorganisms of a peptidase activity and/or of a variation in pH, characterized in that it comprises, or consists of, the following steps:

a) providing a detecting and/or identifying medium comprising a compound of the following formula (I):

(I)

according to which:
$Y_1$ is a peptide, H or an alkyl;
$W_1$, $W_2$, $W_3$ and $W_4$ are independently H, Br, Cl, F, I, alkyl, alkoxy, thiomethyl, perfluoroalkyl, nitro, cyano, carboxyl (including the esters or amides thereof) or any combination thereof;
n=0, 1 or 2;
U is N or $N^+R$ and V is $CZ_6N$ or $N^+R$ or else V is N or $N^+R$ and U is $CZ_6$;
R is H, alkyl, aralkyl, aryl, alkanoyl or alkylsulfonyl;
$Z_1$, $Z_2$, $Z_3$, $Z_4$ and $Z_5$ are independently H, Br, Cl, F, I, alkyl, aryl, alkoxy, perfluoroalkyl, nitro, cyano, carboxyl, sulfonyl, including the carboxyl or sulfonyl esters or amides,
and salts thereof, b) inoculating the medium with a biological sample to be tested,
c) leaving to incubate, and
d) revealing the presence of at least one peptidase activity or a variation in pH.

When said method is a method for detecting only a variation in pH, $Y_1$ is H or an alkyl.

When said method is a method for the detection in microorganisms of a peptidase activity, $Y_1$ is a peptide. Preferentially U or V is N.

When said method is a method for the detection in microorganisms of a peptidase activity and of a variation in pH, $Y_1$ is a peptide. Preferentially U or V is N.

According to one preferred embodiment of the invention, $Y_1$ is a peptide, preferentially chosen from alanine, asparagine, glutamine, and tyrosine.

According to one preferred embodiment of the invention, n=1.

According to one preferred embodiment of the invention, $W_1$, $W_2$, $W_3$ and $W_4$ are independently H.

According to one preferred embodiment of the invention, U is CH and V is N or $N^+R$, preferentially $N^+CH_3$.

According to one preferred embodiment of the invention, V is CH and U is N or $N^+R$, preferentially $N^+CH_3$.

According to one preferred embodiment of the invention, $Z_1$, $Z_2$, $Z_3$, $Z_4$, $Z_5$ and $Z_6$ are independently H.

According to one preferred embodiment of the invention, L-alanyl-4-(4'-amidophenyl)-2-methylquinoline, L-alanyl-4-(4'-amidostyryl)-N-benzylquinolinium TFA, L-glutamyl-4-(4'-amidostyryl)-N-benzylquinolinium TFA, beta-alanyl-4-(4'-amidostyryl)-N-benzylquinolinium TFA, L-alanyl-4-

(4'-amidostyryl)-N-methylquinolinium TFA, D-alanine-N-methyl-4-(4'-aminostyryl)quinolinium (dichloride), L-alanyl-2-(4'-amidostyryl)-N-methylquinolinium, Z-alanyl-2-(4'-amidostyryl)-N-methylquinolinium, L-alanyl-4-(4'-amidostyryl)-N-methylquinolinium (dichloride), L-alanyl-L-alanyl-4-(4'-amidostyryl)-N-methylquinolinium (dichloride), L-alanyl-L-alanyl-L-alanyl-4-(4'-amidostyryl)-N-methylquinolinium (dichloride), γ-aminobutyryl-4-(4'-amidostyryl)-N-methylquinolinium di-Cl, L-asparaginyl-4-(4'-amidostyryl)-N-methylquinolinium-bis-TFA, -aspartyl-4-(4'-amidostyryl)-N-methylquinolinium dichloride, β-aspartyl-4-(4'-amidostyryl)-N-methylquinolinium dichloride, glycyl-4-(4'-amidostyryl)-N-methylquinolinium (dichloride), L-gamma-glutamyl-4-(4'-amidostyryl)-N-methylquinolinium (dichloride), glycyl-4-(4'-amidostyryl)-N-methylquinolinium chloride, L-leucyl-4-(4'-amidostyryl)-N-methylquinolinium dihydrochloride, L-methionyl-4-(4'-amidostyryl)-N-methylquinolinium di-Cl, pyroglutamyl-4-(4'-amidostyryl)-N-methylquinolinium iodide, sarcosinyl-4-(4'-amidostyryl)-N-methylquinolinium dichloride, L-tryptophanyl-4-(4-amidostyryl)-N-methylquinolinium dihydrochloride, L-tyrosyl-4-(4'-amidostyryl)-N-methylquinolinium dihydrochloride, beta-alanyl-2-(4'-amidostyryl)-N-methylquinolinium TFA, L-prolyl-2-(4'-amidostyryl)-N-methylquinolinium (HBr), Z-arginyl-2-(4'-amidostyryl)-N-methylquinolinium, L-pyroglutamyl-2-(4'-amidostyryl)-N-methylquinolinium, L-alanyl-4-(4'-amidostyryl)quinoline TFA, β-alanyl-4-(4'-amidostyryl)quinoline, L-glutamyl-4-(4'-amidostyryl)quinoline TFA, glycyl-4-(4'-amidostyryl)quinoline TFA, pyroglutamyl-4-(4'-amidostyryl)quinoline, L-alanyl-2-(4'-amidostyryl)quinoline, (3-alanyl-2-(4'-amidostyryl)quinoline, glycyl-2-(4'-amidostyryl)quinoline TFA, L-alanyl-2-(2'-pyridyl)-4-(4"-amidostyryl)quinoline.

According to one preferred embodiment of the invention, said compound is chosen from: β-alanyl-2-(4'-amidostyryl)quinoline (β-Ala-ASQ), L-tyrosyl-4-(4'-amidostyryl)-N-methylquinolinium dihydrochloride (Tyr-ASQM⁺), L-asparaginyl-4-(4'-amidostyryl)-N-methylquinolinium-bis-TFA (Asn-ASQM⁺), L-gamma-glutamyl-4-(4'-amidostyryl)-N-methylquinolinium (dichloride) (λ-Glu-ASQM⁺), and L-alanyl-L-alanyl-L-alanyl-4-(4'-amidostyryl)-N-methylquinolinium (dichloride) (Tri-Ala-ASQM⁺).

The inoculation of the microorganisms can be carried out by any of the inoculation techniques known to those skilled in the art. An incubation step can be carried out at a temperature for which the enzymatic activity that it is desired to detect is optimal, which those skilled in the art can readily choose according to the enzymatic activity to be detected. Step d) can be carried out by visual examination or by colorimetry or fluorimetry. During step d), it is possible to reveal the presence of the peptidase activity or the variation in pH, alone or in combination with at least one other enzymatic activity.

Preferentially, the microorganism is chosen from *Escherichia coli, Serratia marcescens, Enterobacter cloacae, Salmonella typhimurium, Providencia rettgeri, Yersinia enterocolitica, Pseudomonas aeruginosa, Bacillus subtilis, Listeria monocytogenes, Staphylococcus aureus, Streptococcus pyogenes* and *Enterococcus faecalis*.

The invention also relates to a method for differentiating bacteria in terms of whether they belong to Gram-positive bacteria or to Gram-negative bacteria, characterized in that it comprises the following steps:
a) providing a detecting and/or identifying medium comprising a compound of the following formula (I), as an enzyme substrate for the detection of a peptidase activity and/or of a variation in pH:

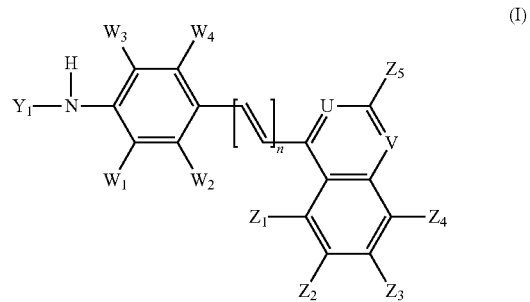

according to which:
Y₁ is a peptide, H or an alkyl;
W₁, W₂, W₃ and W₄ are independently H, Br, Cl, F, I, alkyl, alkoxy, thiomethyl, perfluoroalkyl, nitro, cyano, carboxyl (including the esters or amides thereof) or any combination thereof;
n=0, 1 or 2;
U is N or N⁺R and V is CZ₆N or N⁺R or else V is N or N⁺R and U is CZ₆;
R is H, alkyl, aralkyl, aryl, alkanoyl or alkylsulfonyl;
Z₁, Z₂, Z₃, Z₄, and Z₅ are independently H, Br, Cl, F, I, alkyl, aryl, alkoxy, perfluoroalkyl, nitro, cyano, carboxyl, sulfonyl, including the carboxyl or sulfonyl esters or amides,
and salts thereof,
b) inoculating the medium with a biological sample to be tested,
c) leaving to incubate, and
d) revealing the presence of at least one peptidase activity.

When said medium is a medium for detecting only a sole variation in pH, Y₁ is H or an alkyl.

When said medium is a medium for detecting a peptidase activity, Y₁ is a peptide. Preferentially U or V is N.

When said medium is a medium for detecting a peptidase activity and a variation in pH, Y₁ is a peptide. Preferentially U or V is N.

As indicated above, the inoculation of the microorganisms can be carried out by any of the inoculation techniques known to those skilled in the art. An incubation step can be carried out at a temperature for which the enzymatic activity that it is desired to detect is optimal, which those skilled in the art can readily choose according to the enzymatic activity to be detected. Step d) can be carried out by visual examination or by colorimetry or fluorimetry. During step d), it is possible to reveal the presence of the peptidase activity, alone or in combination with other enzymatic activities. In certain cases, it may be advantageous to perform step d) in the presence of an acid, such as acetic acid.

According to one preferred embodiment of the invention, Y₁ is a peptide, preferentially chosen from alanine, asparagine, glutamine, and tyrosine.

According to one preferred embodiment of the invention, n=1.

According to one preferred embodiment of the invention, W₁, W₂, W₃ and W₄ are independently H.

According to one preferred embodiment of the invention, U is CH and V is N or N⁺R, preferentially N⁺CH₃.

According to one preferred embodiment of the invention, V is CH and U is N or N⁺R, preferentially N⁺CH₃.

According to one preferred embodiment of the invention, Z₁, Z₂, Z₃, Z₄, Z₅ and Z₆ are independently H.

According to one preferred embodiment of the invention, L-alanyl-4-(4'-amidophenyl)-2-methylquinoline, L-alanyl-4-(4'-amidostyryl)-N-benzylquinolinium TFA, L-glutamyl-4-(4'-amidostyryl)-N-benzylquinolinium TFA, beta-alanyl-4-(4'-amidostyryl)-N-benzylquinolinium TFA, L-alanyl-4-(4'-amidostyryl)-N-methylquinolinium TFA, D-alanine-N- methyl-4-(4'-aminostyryl)quinolinium (dichloride), L-alanyl-2-(4'-amidostyryl)-N-methylquinolinium, Z-alanyl-2-(4'-amidostyryl)-N-methylquinolinium, L-alanyl-4-(4'-amidostyryl)-N-methylquinolinium (dichloride), L-alanyl-L-alanyl-4-(4'-amidostyryl)-N-methylquinolinium (dichloride), L-alanyl-L-alanyl-L-alanyl-4-(4'-amidostyryl)-N-methylquinolinium (dichloride), γ-aminobutyryl-4-(4'-amidostyryl)-N-methylquinolinium di-Cl, L-asparaginyl-4-(4'-amidostyryl)-N-methylquinolinium-bis-TFA, -aspartyl-4-(4'-amidostyryl)-N-methylquinolinium dichloride, β-aspartyl-4-(4'-amidostyryl)-N-methylquinolinium dichloride, glycyl-4-(4'-amidostyryl)-N-methylquinolinium (dichloride), L-gamma-glutamyl-4-(4'-amidostyryl)-N-methylquinolinium (dichloride), glycyl-4-(4'-amidostyryl)-N-methylquinolinium chloride, L-leucyl-4-(4'-amidostyryl)-N-methylquinolinium dihydrochloride, L-methionyl-4-(4'-amidostyryl)-N-methylquinolinium di-Cl, pyroglutamyl-4-(4'-amidostyryl)-N-methylquinolinium iodide, sarcosinyl-4-(4'-amidostyryl)-N-methylquinolinium dichloride, L-tryptophanyl-4-(4-amidostyryl)-N-methylquinolinium dihydrochloride, L-tyrosyl-4-(4'-amidostyryl)-N-methylquinolinium dihydrochloride, beta-alanyl-2-(4'-amidostyryl)-N-methylquinolinium TFA, L-prolyl-2-(4'-amidostyryl)-N-methylquinolinium (HBr), Z-arginyl-2-(4'-amidostyryl)-N-methylquinolinium, L-pyroglutamyl-2-(4'-amidostyryl)-N-methylquinolinium, L-alanyl-4-(4'-amidostyryl)quinoline TFA, (3-alanyl-4-(4'-amidostyryl)quinoline, L-glutamyl-4-(4'-amidostyryl)quinoline TFA, glycyl-4-(4'-amidostyryl)quinoline TFA, pyroglutamyl-4-(4'-amidostyryl)quinoline, L-alanyl-2-(4'-amidostyryl)quinoline, β-alanyl-2-(4'-amidostyryl)quinoline, glycyl-2-(4'-amidostyryl)quinoline TFA, L-alanyl-2-(2'-pyridyl)-4-(4''-amidostyryl)quinoline.

According to one preferred embodiment of the invention, said compound is chosen from: β-alanyl-2-(4'-amidostyryl)quinoline (β-Ala-ASQ), L-tyrosyl-4-(4'-amidostyryl)-N-methylquinolinium dihydrochloride (Tyr-ASQM$^+$), L-asparaginyl-4-(4'-amidostyryl)-N-methylquinolinium-bis-TFA (Asn-ASQM$^+$), L-gamma-glutamyl-4-(4'-amidostyryl)-N-methylquinolinium (dichloride) (λ-Glu-ASQM$^+$), and L-alanyl-L-alanyl-L-alanyl-4-(4'-amidostyryl)-N-methylquinolinium (dichloride) (Tri-Ala-ASQM$^+$).

Preferentially, the microorganism is chosen from *Escherichia coli, Serratia marcescens, Enterobacter cloacae, Salmonella typhimurium, Providencia rettgeri, Yersinia enterocolitica, Pseudomonas aeruginosa, Bacillus subtilis, Listeria monocytogenes, Staphylococcus aureus, Streptococcus pyogene* and *Enterococcus faecalis*.

The invention also relates to a medium for detecting and/or identifying microorganisms, comprising a compound of the following formula (I) for detecting a peptidase activity and/or a variation in pH:

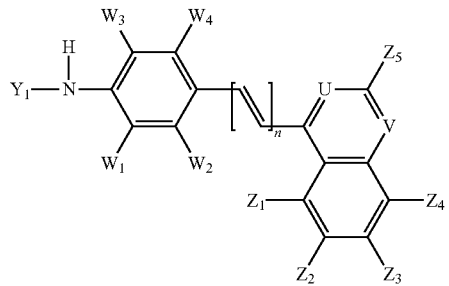

according to which:
Y$_1$ is a peptide, H or an alkyl;
W$_1$, W$_2$, W$_3$ and W$_4$ are independently H, Br, Cl, F, I, alkyl, alkoxy, thiomethyl, perfluoroalkyl, nitro, cyano, carboxyl (including the esters or amides thereof) or any combination thereof;

n=0, 1 or 2;
U is N or N$^+$R and V is CZ$_6$N or N$^+$R or else V is N or N$^+$R and U is CZ$_6$;
R is H, alkyl, aralkyl, aryl, alkanoyl or alkylsulfonyl;
Z$_1$, Z$_2$, Z$_3$, Z$_4$, and Z$_5$ are independently H, Br, Cl, F, I, alkyl, aryl, alkoxy, perfluoroalkyl, nitro, cyano, carboxyl, sulfonyl, including the carboxyl or sulfonyl esters or amides,
and salts thereof.

When said medium is a medium for detecting a sole variation in pH, Y$_1$ is H or an alkyl.

When said medium is a medium for detecting a peptidase activity, and optionally a variation in pH, Y$_1$ is a peptide. Preferentially U or V is N.

According to one preferred embodiment of the invention, Y$_1$ is a peptide, preferentially chosen from alanine, asparagine, glutamine, and tyrosine.

According to one preferred embodiment of the invention, n=1.

According to one preferred embodiment of the invention, W$_1$, W$_2$, W$_3$ and W$_4$ are independently H.

According to one preferred embodiment of the invention, U is CH and V is N or N$^+$R, preferentially N$^+$CH$_3$.

According to one preferred embodiment of the invention, V is CH and U is N or N$^+$R, preferentially N$^+$CH$_3$.

According to one preferred embodiment of the invention, Z$_1$, Z$_2$, Z$_3$, Z$_4$, Z$_5$ and Z$_6$ are independently H.

According to one preferred embodiment of the invention, L-alanyl-4-(4'-amidophenyl)-2-methylquinoline, L-alanyl-4-(4'-amidostyryl)-N-benzylquinolinium TFA, L-glutamyl-4-(4'-amidostyryl)-N-benzylquinolinium TFA, beta-alanyl-4-(4'-amidostyryl)-N-benzylquinolinium TFA, L-alanyl-4-(4'-amidostyryl)-N-methylquinolinium TFA, D-alanine-N-methyl-4-(4'-aminostyryl)quinolinium (dichloride), L-alanyl-2-(4'-amidostyryl)-N-methylquinolinium, Z-alanyl-2-(4'-amidostyryl)-N-methylquinolinium, L-alanyl-4-(4'-amidostyryl)-N-methylquinolinium (dichloride), L-alanyl-L-alanyl-4-(4'-amidostyryl)-N-methylquinolinium (dichloride), L-alanyl-L-alanyl-L-alanyl-4-(4'-amidostyryl)-N-methylquinolinium (dichloride), γ-aminobutyryl-4-(4'-amidostyryl)-N-methylquinolinium di-Cl, L-asparaginyl-4-(4'-amidostyryl)-N-methylquinolinium-bis-TFA, -aspartyl-4-(4'-amidostyryl)-N-methylquinolinium dichloride, β-aspartyl-4-(4'-amidostyryl)-N-methylquinolinium dichloride, glycyl-4-(4'-amidostyryl)-N-methylquinolinium (dichloride), L-gamma-glutamyl-4-(4'-amidostyryl)-N-methylquinolinium (dichloride), glycyl-4-(4'-amidostyryl)-N-methylquinolinium chloride, L-leucyl-4-(4'-amidostyryl)-N-methylquinolinium dihydrochloride, L-methionyl-4-(4'-amidostyryl)-N-methylquinolinium di-Cl, pyroglutamyl-4-(4'-amidostyryl)-N-methylquinolinium iodide, sarcosinyl-4-(4'-amidostyryl)-N-methylquinolinium dichloride, L-tryptophanyl-4-(4-amidostyryl)-N-methylquinolinium dihydrochloride, L-tyrosyl-4-(4'-amidostyryl)-N-methylquinolinium dihydrochloride, beta-alanyl-2-(4'-amidostyryl)-N-methylquinolinium TFA, L-prolyl-2-(4'-amidostyryl)-N-methylquinolinium (HBr), Z-arginyl-2-(4'-amidostyryl)-N-methylquinolinium, L-pyroglutamyl-2-(4'-amidostyryl)-N-methylquinolinium, L-alanyl-4-(4'-amidostyryl)quinoline TFA, β-alanyl-4-(4'-amidostyryl)quinoline, L-glutamyl-4-(4'-amidostyryl)quinoline TFA, glycyl-4-(4'-amidostyryl)quinoline TFA, pyroglutamyl-4-(4'-amidostyryl)quinoline, L-alanyl-2-(4'-amidostyryl)quinoline, β-alanyl-2-(4'-amidostyryl)quinoline, glycyl-2-(4'-amidostyryl)quinoline TFA, L-alanyl-2-(2'-pyridyl)-4-(4''-amidostyryl)quinoline.

According to one preferred embodiment of the invention, said compound is chosen from: β-alanyl-2-(4'-amidostyryl) quinoline (β-Ala-ASQ), L-tyrosyl-4-(4'-amidostyryl)-N-methylquinolinium dihydrochloride (Tyr-ASQM$^+$), L-asparaginyl-4-(4'-amidostyryl)-N-methylquinolinium-bis-TFA (As n-ASQM$^+$), L-gamma-glutamyl-4-(4'-amidostyryl)-N-methylquinolinium (dichloride) (λ-Glu-ASQM$^+$), and L-alanyl-L-alanyl-L-alanyl-4-(4'-amidostyryl)-N-methylquinolinium (dichloride) (Tri-Ala-ASQM$^+$).

Preferentially, the microorganism is chosen from *Escherichia coli, Serratia marcescens, Enterobacter cloacae, Salmonella typhimurium, Providencia rettgeri, Yersinia enterocolitica, Pseudomonas aeruginosa, Bacillus subtilis, Listeria monocytogenes, Staphylococcus aureus, Streptococcus pyogenes* and *Enterococcus faecalis*.

Preferentially, said reaction medium is a medium for detecting and/or identifying microorganisms, said medium comprising at least one molecule used as an enzyme substrate or a pH indicator as defined above.

Preferentially, said compound, enzyme substrate or pH indicator, is at a concentration of between 1 and 1000 mg/l, preferably between 10 and 500 mg/l.

According to one particular embodiment of the invention, said detecting and/or identifying medium according to the invention also comprises at least one other enzyme substrate, specific for an enzymatic activity other than the peptidase activity detected by the molecule according to the invention.

According to another particular embodiment of the invention, said detecting and/or identifying medium according to the invention also comprises at least one substrate specific for an enzymatic activity other than that demonstrated by the variation in pH. The enzymatic metabolism of the other substrate(s) generates a detectable signal, which is different from the signal generated by the compound according to the invention used as an enzyme substrate or as a pH indicator, for instance different colored or fluorescent products, for enabling the demonstration, such as the detection and/or the identification and/or the quantification, or one or more microorganisms. As other specific substrate, any other substrate conventionally used in the detection of microorganisms may be used. The concentration of the other specific enzyme substrate is generally between 0.01 and 1 g/l. Those skilled in the art will be able readily to determine such a concentration according to the substrate used. By way of indication, it is possible to combine the compounds according to the invention with peptidase, osidase, esterase or reductase enzyme substrates. In particular, it is possible to combine a substrate according to the invention for which the peptide is a β-alanine with an osidase substrate, such as 5-bromo-4-chloro-3-indolyl-β-glucoside, or alizarin-β-galactoside. It is also possible to combine a substrate according to the invention for which the peptide is L-alanine with an esterase substrate, such as 5-bromo-6-chloro-3-indoxyl octanoate or 5-bromo-3-indoxyl phosphate.

According to one particular embodiment of the invention, said detecting and/or identifying medium according to the invention also comprises at least one other enzyme substrate specific for the peptidase activity or specific for the enzymatic activity detected by a compound according to the invention used as a pH indicator. Through the particular choice of substrates, it is therefore possible to identify groups of microorganisms expressing the same enzymatic activity. The concentration of other specific enzyme substrate is generally between 0.01 and 1 g/l. Those skilled in the art will be able to readily determine such a concentration according to the substrate used. In particular, it is possible to combine a substrate according to the invention for which the peptide is an L-alanine with an L-alanine aminopeptidase substrate described in application WO 2006030119, such as L-alanine-pentyl-resorufamine.

According to one particular embodiment of the invention, said detecting and/or identifying medium according to the invention also comprises at least one metabolic indicator, specific for a metabolic activity other than that detected by the compound according to the invention used as a substrate or as a pH indicator.

This metabolic indicator can in particular be a carbon or nitrogen source optionally combined with a reagent which reveals its metabolism. According to one particular embodiment, the carbon or nitrogen source is combined with a pH indicator other than the compound according to the invention used in this respect. According to another particular embodiment, the carbon or nitrogen source is combined with a cation. According to another particular embodiment, the metabolic indicator makes it possible to detect a tryptophanase activity and combines tryptophan and a reagent which makes it possible to detect the production of indole.

The examples hereinafter are given by way of illustration.

EXAMPLE 1

Substrate Synthesis 4-(4'-Aminostyryl)quinoline was prepared according to the method of Bahner et al. (C. T. Bahner, C. Cook, J. Dale, J. Fain, F. Hannan, P. Smith and J. Wilson, Journal of Organic Chemistry, 1958, 23, 1060-1062).

The aminoacylation of 4-(4'-aminostyryl)quinoline with t-BOC-β-alanine is given by way of example, and the other aminoacylations were carried out in the same way with another protected amino acid.

Synthesis of the t-BOC-β-alanine-4-(4'-aminostyryl) quinoline from 4-(4'-aminostyryl) quinoline and t-BOC-β-alanine according to the mixed anhydride method First and foremost, care was taken to ensure that all the glassware used was completely dry since the presence of moisture could have prevented the reaction from taking place correctly. 0.50 g (0.00266 mol) of t-Boc-L-alanine was dissolved in 10 ml of dry tetrahydrofuran (THF) and a $CaCl_2$ trap was added to the neck of the round-bottomed flask in order to ensure that it was leaktight. The mixture was stirred magnetically and the temperature of the reaction medium was brought down to −15° C. using a bath of frozen ice mixed with NaCl salts. Once this temperature had been reached, stirring was carried out for a further 5 minutes. 0.34 g (0.0033 mol) of N-methylmorpholine was then added, with great care being taken to ensure that the temperature went back down to −15° C. before proceeding with the next step. 0.36 g (0.00266 mol) of isochlorobutyl formate was then added dropwise with the greatest care, the reaction medium became cloudy as anticipated with each drop added. A few minutes later, 0.49 g (0.002 mol) of 4-(4'-aminostyryl)quinoline was dissolved in the minimum amount of dry THF and was added to the reaction medium. The ice bath was removed after 2 hours and the reaction medium was left to stir overnight. The solution was filtered, the round-bottomed flask was rinsed with normal THF and the filtrate was kept. A slight precipitate was present, the next step was therefore carried out, otherwise it would have been necessary to place the solution in a clean, round-bottomed flask and to evaporate-off the appropriate amount of solvent. The solution was transferred using a Pasteur pipette, into a 400 ml beaker containing ice, water and also sodium carbonate ($Na_2CO_3$). The whole was left to stir for a couple of hours, until a clear solution was obtained. The solution was filtered in a small Buchner funnel and then the precipitate was dissolved in ethanol in order to recrystallize it. 0.76 g of t-BOC-β-alanine-4-(4'-aminostyryl)quinoline, a yellow solid, was thus obtained with a yield of 90%, m.p. 160-162° C. HRMS (EI) for $C_{25}H_{25}N_3O_3$. Theoretical mass of the molecular ion 418.2125 $(M+H)^+$. Mass found: 418.2123. $^1$H-NMR: (DMSO) δ 1.34 (9H, s, $C(CH_3)_3$), 3.19 (2H, q, J=5.94 Hz, >$CH_2$), 3.38 (2H, m, >$CH_2$), 6.88 (1H, t, J=5.69 Hz, NH), 7.50 (1H, d, J=16.08 Hz, =CH), 7.61 (1H, m, Ph-H), 7.64 (2H, d, J=8.66 Hz, C6'-H and C2'-H), 7.73 (1H, m, Ph-H), 7.74 (2H, d, J=8.91 Hz, C5'-H and C3'-H), 7.79 (1H, d, J=4.70 Hz, C3-H), 7.96 (1H, d, J=6.33 Hz, =CH), 7.99 (1H, d, J=8.16 Hz, C5-H), 8.48 (1H, d, J=8.41 Hz, C8-H), 8.82 (1H, d, J=4.70 Hz, C2-H), 10.09 (1H, s, NH). IR: $v_{max}$ cm$^{-1}$ 3380 (CO), 3307 (CONH), 1693 (CONH), 1673 (CONH), 1365 ($C(CH_3)_3$), 754 ($CH_2$).

The deprotection of the t-BOC-amino acid compounds was accomplished either by reaction with HCl (giving a hydrochloric acid salt) or by reaction with acid TFA (giving a trifluoroacetic acid salt). The deprotection of t-BOC-β-alanine-4-(4'-aminostyryl)quinoline with HCl is given by way of example, and the other deprotections were carried out in the same way. For the deprotection with TFA, the compound to be deprotected was placed in a round-bottomed flask fitted with a $CaCl_2$ trap. Trifluoroacetic acid was then added and the mixture was left to stir magnetically overnight. The TFA was evaporated off in order to obtain the product in trifluoroacetic acid salt form.

Synthesis of β-alanine-4-(4'-aminostyryl)quinoline from t-BOC-β-alanine-4-(4'-aminostyryl)quinoline t-BOC-β-alanine-4-(4'-aminostyryl)quinoline was dissolved in the minimum amount of ethyl acetate in a round-bottomed flask fitted with a $CaCl_2$ trap. A saturated solution of HCl in ethyl acetate was then added. The mixture was left to stir overnight and then the solvent was evaporated off. Dichloric β-alanine-4-(4'-aminostyryl)quinoline, a brown solid, was thus obtained with a yield of 77%, m.p. 176-178° C. HRMS (EI) for $C_{20}H_{19}N_3O$. Theoretical mass of the molecular ion 318.1601 $(M+H)^+$. Mass found: 318.1601. $^1$H-NMR: (DMSO) δ 2.50 (2H, t, J=6.19 Hz, >$CH_2$), 3.15 (2H, m, >$CH_2$), 7.27 (1H, d, J=2.72 Hz, Ph-H), 7.30 (1H, d, J=16.08 Hz, =CH), 7.57 (2H, d, J=8.41 Hz, Ph-H), 7.63 (1H, d, J=16.08 Hz, —CH), 7.64 (2H, d, J=8.91 Hz, Ph-H), 7.74 (2H, m, Ph-H), 8.12 (1H, d, J=8.66 Hz, Ph-H), 8.23 (1H, d, J=7.42 Hz, C8-H), 8.88 (1H, d, J=4.45 Hz, C2-H), 10.43 (1H, s, NH). IR: $v_{max}$ cm$^{-1}$ 2852 (NH salt), 1674 (C=O), 1584 (NH), 1379 (NH).

The alkylation of the t-BOC-amino acid compounds was carried out by reaction with a haloalkyl. The salts thus obtained were deprotected either with HCl or with acid TFA as mentioned above. The methylation and the deprotection of the t-BOC-β-alanine-4-(4'-aminostyryl)quinoline with methyl iodide is given by way of example.

Synthesis of the dichlorinated β-alanine-N-methyl-4-(4'-aminostyryl)quinolinium from t-BOC-β-alanine-4-(4'-aminostyryl)quinoline A mixture of 0.42 g (0.001 mol) of t-Boc-β-alanyl-4-(4'-aminostyryl)quinoline and 2.21 g (0.0155 mol) of methyl iodide in 10 ml of acetonitrile was stirred overnight. The mixture was filtered, giving 0.38 g of an orange solid of t-Boc-β-alanyl-N-methyl-4-(4'-aminostyryl)quinolinium iodide with a yield of 70%, 180-182° C. HRMS (EI) for $C_{26}H_{29}N_3O_3$. Theoretical mass of the molecular ion 432.2282 $(M+H)^+$. Mass found: 432.2280. $^1$H-NMR: (DMSO) δ 1.39 (9H, s, —$C(CH_3)_3$), 3.24 (2H, quartet, J=6.19 Hz, >$CH_2$), 3.37 (2H, m, >$CH_2$), 4.54 (3H, s, —$CH_3$), 6.95 (1H, t, J=6.19 Hz, NH), 7.75 (2H, d, J=8.66 Hz, C6'-H and C2'-H), 7.96 (2H, d, J=8.66 Hz, C5'-H and C3'-H), 8.05 (1H, t, J=7.42 Hz, C7-H), 8.08 (1H, d, J=16.08 Hz, =CH), 8.24 (1H, d, J=16.08 Hz, =CH), 8.27 (1H, t, J=6.93 Hz, C6-H), 8.44 (1H, d, J=8.91 Hz, C5-H), 8.48 (1H, d, J=6.68 Hz, C3-H), 9.05 (1H, d, J=8.66 Hz, C8-H), 9.32 (1H, d, J=6.68 Hz, C2-H), 10.26 (1H, s, NH). IR: $v_{max}$ cm$^{-1}$ 3368 (NH), 3276 (NH), 1674 (CO), 1617 (CO), 1592 (CONH), 1571 (CONH), 1365 ($CCH_3)_3$), 1395 ($CH_3$).

0.54 g (0.0013 mol) of this compound was deprotected with HCl, giving 0.39 g of a brown solid of dichlorinated β-alanine-N-methyl-4-(4'-aminostyryl)quinolinium with a yield of 77%, m.p. 176-178° C. HRMS (EI) for $C_{20}H_{19}N_3O$. Theoretical mass of the molecular ion 318.1601 $(M+H)^+$. Mass found: 318.1601. $^1$H-NMR: (DMSO) δ 2.50 (2H, t, J=6.19 Hz, >$CH_2$), 3.15 (2H, m, >$CH_2$), 7.27 (1H, d, J=2.72 Hz, Ph-H), 7.30 (1H, d, J=16.08 Hz, =CH), 7.57 (2H, d, J=8.41 Hz, Ph-H), 7.63 (1H, d, J=16.08 Hz, —CH), 7.64 (2H, d, J=8.91 Hz, Ph-H), 7.74 (2H, m, Ph-H), 8.12 (1H, d, J=8.66 Hz, Ph-H), 8.23 (1H, d, J=7.42 Hz, C8-H), 8.88 (1H, d, J=4.45 Hz, C2-H), 10.43 (1H, s, NH). IR: $v_{max}$ cm$^{-1}$ 2852 (NH salt), 1674 (C=O), 1584 (NH), 1379 (NH).

Other examples of typical substrates obtained in a manner similar to that mentioned above:

Dichlorinated L-alanine-N-methyl-4-(4'-aminostyryl)quinolinium, a red solid, m.p. 244-246° C. HRMS (EI) for $C_{21}H_{23}N_3O$. Theoretical mass of the molecular ion 332.1757 $(M-2HCl+H)^+$. Mass found: 332.1756. $^1$H-NMR: (DMSO) δ 1.51 (3H, d, J=6.93 Hz, —$CH_3$), 4.19 (1H, q, J=6.93 Hz, ala-H), 4.55 (3H, s, —$CH_3$), 7.86 (2H, d, J=8.66 Hz, C6'-H and C2'-H), 8.01 (2H, d, J=8.66 Hz, C5'-H and C3'-H), 8.05 (1H, m, Ph-H), 8.28 (1H, m, Ph-H), 8.16 (1H, d, J=16.08 Hz, =CH), 8.29 (1H, d, J=16.08 Hz, =CH), 8.44 (1H, d, J=8.91 Hz, C5-H), 8.51 (1H, d, J=6.68 Hz, C3-H), 9.06 (1H, d, J=8.41 Hz, C8-H), 9.40 (1H, d, J=6.68 Hz, C2-H), 11.49 (1H, s, NH). IR: $v_{max}$ cm$^{-1}$ 1693 (C=O), 1597 (NH), 1533 (NH), 1324 (NH), 1369 ($CH_3$).

Dichlorinated L-gamma-glutamyl-N-methyl-4-(4'-aminostyryl)quinolinium.

$^1$H-NMR: (DMSO) δ 2.05 (2H, m, >$CH_2$), 2.55 (2H, m, >$CH_2$), 3.87 (1H, m, >CH—), 4.49 (3H, s, N—$CH_3$), 7.70 (2H, d, J=7 Hz, Ar—H), 7.90 (2H, d, J=7 Hz, Ar—H), 7.90-8.50 (6H, m, Ar—H, —CH=), 8.60 (1H, broad s, >NH), 8.97 (1H, d, J=8 Hz, Ar—H), 9.29 (1H, d, J=5 Hz, Ar—H).

Dichlorinated L-tyrosyl-N-methyl-4-(4'-aminostyryl)quinolinium.

$^1$H-NMR: (DMSO) δ 3.10 (2H, m, >$CH_2$), 4.30 (1H, m, >CH—), 4.52 (3H, s, N—$CH_3$), 6.70 (2H, d, J=7 Hz, Ar—H), 7.12 (2H, d, J=7 Hz, Ar—H), 7.79 (2H, d, J=7 Hz, Ar—H), 7.98 (2H, d, J=7 Hz, Ar—H), 8.00-8.60 (6H, m, Ar—H and —CH=), 9.04 (1H, d, J=7 Hz, Ar—H), 9.38 (1H, d, J=5 Hz, Ar—H), 9.46 (1H, broad s, >OH).

Dichlorinated L-alanine-N-methyl-4-(4'-aminostyryl)quinolinium and D-alanine-N-methyl-4-(4'-aminostyryl)quinolinium.

$^1$H-NMR: (DMSO) δ 1.51 (3H, d, J=6.93 Hz, —$CH_3$), 4.19 (1H, q, J=6.93 Hz, ala-H), 4.55 (3H, s, —$CH_3$), 7.86 (2H, d, J=8.66 Hz, C6'-H and C2'-H), 8.01 (2H, d, J=8.66 Hz, C5'-H and C3'-H), 8.05 (1H, m, Ph-H), 8.28 (1H, m, Ph-H), 8.16 (1H, d, J=16.08 Hz, =CH), 8.29 (1H, d, J=16.08 Hz, =CH), 8.44 (1H, d, J=8.91 Hz, C5-H), 8.51 (1H, d, J=6.68 Hz, C3-H), 9.06 (1H, d, J=8.41 Hz, C8-H), 9.40 (1H, d, J=6.68 Hz, C2-H), 11.49 (1H, s, NH).

EXAMPLE 2

Use of Substrates of Formula I According to the Invention for Detecting a Peptidase Activity a) Peptidase Substrates The compounds β-alanyl-2-(4'-amidostyryl)quinoline ((3-Ala-ASQ), L-tyrosyl-4-(4'-amidostyryl)-N-methylquinolinium dihydrochloride (Tyr-ASQM$^+$), L-asparaginyl-4-(4'- amidostyryl)-N-methylquinolinium-bis-TFA (Asn-ASQM$^+$), L-gamma-glutamyl-4-(4'-amidostyryl)-N-methylquinolinium (dichloride) (γ-Glu-ASQM$^+$), and L-alanyl-L-alanyl-L-alanyl-4-(4'-amidostyryl)-N-methylquinolinium (dichloride) (Tri-Ala-ASQM$^+$), were synthesized as described in example 1.

b) Preparation of the Medium 40 mg of each of the substrates were dissolved in 4 ml of dimethyl sulfoxide (80 mg for Asn-ASQM$^+$) and added to 400 ml of previously autoclaved Columbia medium. The 6 media were distributed into Petri dishes 90 mm in diameter, in a proportion of 20 ml per dish.

c) Inoculation and Incubation

Seventeen strains of microorganisms stemming from collections and belonging to various species of bacteria and yeasts are inoculated in spots of approximately 10 000 colony-forming units.

Ten microliters of a mixture in equal parts of suspensions at 0.5 McFarland, diluted to 1/20 of the *Escherichia coli* NCTC 10 418 and *Yersinia enterocolitica* NCTC 11 176 strains are inoculated onto the medium by quadrant streaking.

The media are incubated for 24 hours at 37° C., and then the colonies formed are examined visually, with or without the addition of acid and under a UV lamp at 365 nm.

d) Reading of the Results

The results obtained are given in table 1 hereinafter

On the dish seeded with the mixture of 2 strains (*E. coli* and *Y. enterocolitica*), two types of colonies develop: orange colonies of the *E. coli* strain and colorless colonies of the *Y. enterocolitica* strain.

e) Conclusions

On the media according to the invention, it is possible to detect peptidase activities of microorganisms by virtue of the fluorescence or of the coloration of the colonies. With certain substrates according to the invention, the coloration of the colonies appears under acidic conditions, as is the case with β-Ala-ASQ in this example. With the other substrates of this example, the acidification step is not required.

Most commonly, the substrates according to the invention allow the growth of microorganisms of any type: Gram-negative bacteria, Gram-positive bacteria, yeasts, etc., but some can be toxic with respect to certain groups, as is the case of β-Ala-ASQ in this example. By virtue of the various structural variations in the peptidase substrates according to the invention, it is possible to distinguish various groups of microorganisms. Furthermore, since the color does not diffuse in the reaction medium, it is possible to distinguish the cells or colonies expressing the peptidase activity from those not expressing it, and to count said cells or colonies.

| Species Collection number | Tyr-ASQM$^+$ Growth | Color | Tri-Ala-ASQM$^+$ Growth | Color | λ-Glu-ASQM$^+$ Growth | Color | Asn-ASQM$^+$ Growth | Color | β-Ala-ASQ Growth | Fluo. | Color | Color post-acid. |
|---|---|---|---|---|---|---|---|---|---|---|---|---|
| *Escherichia coli* NCTC 10 418 | 2 | Orange | 2 | Orange | 2 | Orange | 2 | Pale orange | 2 | Pale blue | — | Pale yellow |
| *Serratia marcescens* NCTC 10 211 | 2 | Orange | 2 | Orange | 2 | Orange | 2 | Pale orange | 2 | Green | — | Orange |
| *Pseudomonas aeruginosa* NCTC 10 662 | 2 | — | 2 | Orange | 2 | Orange | 2 | Pale orange | 2 | Green | — | Orange |
| *Yersinia enterocolitica* NCTC 11 176 | 2 | Pale orange | 2 | Pale orange | 2 | — | 2 | — | 2 | Pale blue | — | Pale yellow |
| *Salmonella typhimurium* NCTC 74 | 2 | Pale orange | 2 | Orange | 2 | Orange | 2 | — | 2 | Pale blue | — | Pale yellow |
| *Enterobacter cloacae* NCTC 11 936 | 2 | Orange | 2 | Orange | 2 | Orange | 2 | Pale orange | 2 | Pale blue | — | Pale yellow |
| *Providencia rettgeri* NCTC 7 475 | 2 | Pale orange | 2 | Pale orange | 2 | Orange | 2 | — | 2 | Pale blue | — | Pale yellow |
| *Bacillus subtilis* NCTC 9 372 | 1 | — | 2 | — | 1 | — | 2 | Orange | NG | — | — | — |
| *Enterococcus faecalis* NCTC 775 | 1 | Pale orange | 2 | Pale orange | 1 | — | 2 | — | NG | — | — | — |
| *Enterococcus faecium* NCTC 7 171 | 1 | — | 2 | — | 1 | — | 2 | — | NG | — | — | — |
| *Staphylococcus epidermidis* NCTC 11 047 | 0.5 | — | 2 | — | 1 | — | — | — | NG | — | — | — |
| *Staphylococcus aureus* NCTC 6 571 | NG | — | 2 | — | 1 | — | 0.5 | — | NG | — | — | — |
| *Staphylococcus aureus* NCTC 11 939 | NG | — | 2 | — | 1 | — | 2 | Orange | NG | — | — | — |
| *Streptococcus pyogenes* NCTC 8 306 | NG | — | 2 | Pale orange | 1 | — | — | — | NG | — | — | — |
| *Listeria monocytogenes* NCTC 11 994 | 1 | — | 2 | — | 1 | — | 2 | — | NG | — | — | — |
| *Candida albicans* ATCC 90 028 | 0.5 | — | 2 | — | 1 | — | 2 | — | NG | — | — | — |
| *Candida glabrata* NCPF 3 943 | NG | — | 2 | — | 1 | — | 0.5 | — | NG | — | — | — |

NG: No growth,
0.5: weak growth,
1: moderate growth,
2: good growth,
—: no color

EXAMPLE 3

Use of Substrates of Formula I According to the Invention for Detecting a Peptidase Activity a) Peptidase Substrates The pyroglutamyl-4-(4'-amidostyryl)-N-methylquinaldinium iodide compound was synthesized as described in example 1.

b) Preparation of the Medium

A stock solution containing 50 g/l of pyroglutamyl-4-(4'-amidostyryl)-N-methylquinaldinium iodide was prepared in a solvent of DMSO type and added to a Columbia medium previously autoclaved and kept molten, in a proportion of 75 mg/l. After homogenization, this medium was distributed into 120-mm-squared dishes. A medium serving as a growth control (Columbia) and denoted C was also poured.

c) Inoculation and Incubation

Twenty-two strains of microorganisms were inoculated in test spots: 1 µl deposited using bacterial suspensions at 0.5 McFarland ($15 \times 10^4$ CFU/spot).

The media were incubated for 48 hours at 37° C., and then the spots formed were examined visually.

d) Reading of the Results

The results obtained are given in the table hereinafter.

| Strain name Internal ref. | C Growth | Pyroglutamyl-4-(4'-amidostyryl)-N-methylquinaldinium iodide | | |
|---|---|---|---|---|
| | | Growth | Coloration strength | Color |
| Escherichia coli 0002005 | +++ | +++ | – | |
| Serratia marcescens 7303004 | +++ | +++ | ++ | Natural pigment |
| Pseudomonas aeruginosa 0001001 | +++ | +++ | +++ | Orangey-red |
| Burkholderia cepacia 7507032 | ++ | ++ | – | |
| Yersinia enterocolitica 7605019 | ++ | + | – | |
| Salmonella ser. Typhimurium 0801029 | +++ | +++ | – | |
| Citrobacter freundii 0006197 | +++ | +++ | – | |
| Morganella morganii 9207053 | +++ | +++ | – | |
| Enterobacter cloacae 0604040 | +++ | +++ | – | |
| Providencia rettgeri 0706064 | +++ | +++ | – | |
| Klebsiella pneumoniae 0008009 | +++ | +++ | – | |
| Acinetobacter baumannii 0604029 | +++ | +++ | – | |
| Bacillus subtilis 0204038 | +++ | – | – | |
| Enterococcus faecalis 0008192 | ++ | ++ | ++ | – |
| Enterococcus faecium 0610021 | ++ | ++ | ++ | – |
| Staphylococcus epidermidis 0203050 | ++ | – | – | |
| Staphylococcus aureus 7811049 | ++ | ++ | ++ | – |
| MRSA 0303033 | +++ | ++ | – | |
| Streptococcus pyogenes 9806380 | – | – | – | |
| Listeria monocytogenes 8812049 | ++ | ++ | ++ | – |
| Candida albicans 0801025 | ++ | + | – | |
| Candida glabrata 0408083 | + | – | – | |

Legend:
+++: good growth/high coloration strength
++: medium growth/medium coloration strength
+: weak growth/weak coloration strength
–: no growth/no coloration

EXAMPLE 4

Use of Substrates of Formula I According to the Invention for Detecting a Peptidase Activity a. Peptidase Substrates The L-alanyl-4-(4'-amidostyryl)-N-methylquinolinium (dichloride), L-alanyl-L-alanyl-4-(4'-amidostyryl)-N-methylquinolinium (dichloride) and L-alanyl-L-alanyl-L-alanyl-4-(4'-amidostyryl)-N-methylquinolinium (dichloride) compounds were synthesized as described in example 1.

b. Preparation of the Medium

A stock solution at 50 g/l for each of the three substrates was prepared in a solvent of DMSO type and added to a Columbia medium previously autoclaved and kept molten, in a proportion of 75 mg/l. After homogenization, the media were distributed into 120-mm-squared dishes. A medium serving as a growth control (Columbia) and denoted C was also poured.

c. Inoculation and Incubation

Twenty-two strains of microorganisms were inoculated in test spots: depositing of 1 µl using bacterial suspensions at 0.5 McFarland ($15 \times 10^4$ CFU/spot).

The media were incubated for 48 hours at 37° C., and then the spots formed were examined visually.

d. Results

The results obtained are reported in the table hereinafter.

| Strain name | C Growth | L-alanyl-4-(4'-amidostyryl)-N-methylquinolinium (dichloride) | | | L-alanyl-L-alanyl-4-(4'-amidostyryl)-N-methylquinolinium (dichloride) | | | L-alanyl-L-alanyl-L-alanyl-4-(4'-amidostyryl)-N-methylquinolinium (dichloride) | | |
|---|---|---|---|---|---|---|---|---|---|---|
| | | Growth | Coloration strength | Color | Growth | Coloration strength | Color | Growth | Coloration strength | Color |
| Escherichia coli | ++ | ++ | ++ | orange | ++ | – | – | ++ | ++ | orange |

-continued

| Strain name | L-alanyl-4-(4'-amidostyryl)-N-methylquinolinium (dichloride) | | | | L-alanyl-L-alanyl-4-(4'-amidostyryl)-N-methylquinolinium (dichloride) | | | L-alanyl-L-alanyl-L-alanyl-4-(4'-amidostyryl)-N-methylquinolinium (dichloride) | | |
|---|---|---|---|---|---|---|---|---|---|---|
| | C Growth | Growth | Coloration strength | Color | Growth | Coloration strength | Color | Growth | Coloration strength | Color |
| *Serratia marcescens* | ++ | ++ | ++ | orange | ++ | + | orange | ++ | ++ | orange |
| *Pseudomonas aeruginosa* | ++ | ++ | ++ | orange | ++ | − | − | ++ | ++ | orange |
| *Burkholderia cepacia* | ++ | ++ | + | orange | ++ | − | − | ++ | + | orange |
| *Yersinia enterocolitica* | ++ | ++ | ++ | orange | ++ | − | − | ++ | ++ | orange |
| *Salmonella* ser *typhimurium* | ++ | ++ | + | orange | ++ | − | − | ++ | + | orange |
| *Citrobacter freundii* | ++ | ++ | + | orange | ++ | − | − | ++ | + | orange |
| *Morganella morganii* | ++ | ++ | ++ | orange | ++ | − | − | ++ | ++ | orange |
| *Enterobacter cloacae* | ++ | ++ | ++ | orange | ++ | + | orange | ++ | ++ | orange |
| *Providencia rettgeri* | ++ | ++ | + | orange | ++ | − | − | ++ | + | orange |
| *Klebsiella pneumoniae* | ++ | ++ | ++ | orange | ++ | + | orange | ++ | ++ | orange |
| *Acinetobacter baumannii* | ++ | ++ | ++ | orange | ++ | + | orange | ++ | ++ | orange |
| *Bacillus subtilis* | ++ | ++ | − | − | ++ | − | − | ++ | − | — |
| *Enterococcus faecalis* | ++ | ++ | + | orange | ++ | − | − | ++ | + | orange |
| *Enterococcus faecium* | ++ | ++ | − | − | ++ | − | − | ++ | − | — |
| *Staphylococcus epidermidis* | ++ | ++ | ++ | orange | ++ | − | − | ++ | ++ | orange |
| *Staphylococcus aureus* | ++ | ++ | + | orangey-yellow | ++ | − | − | ++ | + | orangey-yellow |
| MRSA | ++ | ++ | + | orange | ++ | − | − | ++ | + | orange |
| *Streptococcus pyogenes* | ++ | ++ | + | orange | ++ | + | orange | ++ | + | orange |
| *Listeria monocytogenes* | ++ | ++ | ++ | orange | ++ | + | orange | ++ | ++ | orange |
| *Candida albicans* | ++ | ++ | − | | + | − | | + | | |
| *Candida glabrata* | + | + | − | | − | − | | − | | |

NB: the internal references of the strains are the same as in example 3.
Legend:
++: medium growth/medium coloration strength
+: weak growth/weak coloration strength
−: no growth/no coloration e. Conclusion The three substrates L-alanyl-4-(4'-amidostyryl)-N-methylquinolinium (dichloride), L-alanyl-L-alanyl-4-(4'-amidostyryl)-N-methylquinolinium (dichloride) and L-alanyl-L-alanyl-L-alanyl-4-(4'-amidostyryl)-N-methylquinolinium (dichloride) make it possible to detect a peptidase activity. The number of amino acids makes it possible to adjust the detection specificity.

EXAMPLE 5

Use of Substrates of Formula I According to the Invention for Detecting a Peptidase Activity a) Peptidase Substrates The L-alanyl-4-(4'-amidostyryl)-N-methylquinolinium (dichloride) and L-alanyl-2-(4'-amidostyryl)-N-methylquinolinium (dichloride) compounds were synthesized as described in example 1.

b) Preparation of the Medium

A stock solution at 50 g/l for each of the two substrates was prepared in a solvent of DMSO type and added to a Columbia medium previously autoclaved and kept molten, in a proportion of 75 mg/l. After homogenization, the media were distributed into Petri dishes 55 mm in diameter. A medium acting as a growth control (Columbia) and denoted C was also poured.

c) Inoculation and Incubation

Twenty-two strains of microorganisms were inoculated with a 10 μl calibrated loop according to the three-quadrant streaking method using bacterial suspensions at 0.5 McFarland.

The media were incubated for 48 hours at 37° C., and then the spots formed were examined visually.

d) Results

The results obtained are reported in the table hereinafter.

|  | | L-alanyl-4-(4'-amidostyryl)-N-methylquinolinium (dichloride) | | | L-alanyl-2-(4'-amidostyryl)-N-methylquinolinium (dichloride) | | |
|---|---|---|---|---|---|---|---|
| Strain name | C Growth | Growth | Coloration strength | Color | Growth | Coloration strength | Color |
| *Escherichia coli* | ++ | ++ | ++ | orange | ++ | − | — |
| *Serratia marcescens* | ++ | ++ | ++ | orange | ++ | + | orange |
| *Pseudomonas aeruginosa* | ++ | ++ | ++ | orange | ++ | − | — |
| *Burkholderia cepacia* | ++ | ++ | − | − | ++ | − | — |
| *Yersinia enterocolitica* | + | + | ++ | orange | + | − | — |
| *Salmonella* ser. typhimurium | ++ | ++ | − | − | ++ | − | — |
| *Citrobacter freundii* | ++ | ++ | ++ | orange | ++ | − | — |
| *Morganella morganii* | ++ | ++ | ++ | orange | ++ | − | — |
| *Enterobacter cloacae* | ++ | ++ | + | orange | ++ | − | — |
| *Providencia rettgeri* | ++ | ++ | ++ | orange | ++ | − | — |
| *Klebsiella pneumoniae* | ++ | ++ | ++ | orange | ++ | − | — |
| *Acinetobacter baumannii* | ++ | ++ | ++ | orange | ++ | − | — |
| *Bacillus subtilis* | ++ | ++ | + | orange | ++ | + | orange |
| *Enterococcus faecalis* | + | + | + | orange | + | + | orange |
| *Enterococcus faecium* | + | + | − | − | + | + | orange |
| *Staphylococcus epidermidis* | ++ | ++ | + | orange | ++ | + | orange |
| *Staphylococcus aureus* | ++ | ++ | + | orange | ++ | − | — |
| MRSA | ++ | ++ | ++ | orange | ++ | + | orange |
| *Streptococcus pyogenes* | + | + | + | orange | + | − | — |
| *Listeria monocytogenes* | + | + | ++ | orange | + | + | orange |
| *Candida albicans* | ++ | ++ | − | − | ++ | − | — |
| *Candida glabrata* | + | + | − | − | + | − | — |

NB: the internal references of the strains are the same as in example 3
Legend:
++: medium growth/medium coloration strength
+: weak growth/weak coloration strength
−: no growth/no coloration e) Conclusion The L-alanyl-4-(4'-amidostyryl)-N-methylquinolinium (dichloride) and L-alanyl-2-(4'-amidostyryl)-N-methylquinolinium (dichloride) compounds make it possible to detect an alanine aminopeptidase activity.

EXAMPLE 6

Use of Substrates of Formula I According to the Invention for Detecting a Variation in pH a) pH Indicators The 4-(4'-aminostyryl)quinoline compound was synthesized as described in example 1.

b) Preparation of the Medium

A stock solution containing 50 g/l of 4-(4'-aminostyryl)quinoline was prepared in a solvent of DMSO type and added to a modified chromID Coli® medium previously autoclaved and kept molten, in a proportion of 50 mg/l. After homogenization, this medium was distributed into 120 mm-squared Petri dishes. A medium acting as a growth control (modified chromID Coli®) and denoted C was also poured.

*Composition of the modified chromID Coli® medium (in g/l):
Peptones: 5.5
Yeast extract: 8
Sodium chloride: 5
Bile salts: 0.7
Glucose: 10
Agar: 12.5 c) Inoculation and Incubation

Forty-four strains of microorganisms (details in the table below) were inoculated in test spots: depositing of 1 µl using bacterial suspensions at 0.5 McFarland ($15 \times 10^4$ CFU/spot).

The media were incubated for 24 hours at 37° C., then the spots formed were examined visually.

|  | Species | API No. |
|---|---|---|
| 1 | *Klebsiella pneumoniae* ssp *pneumoniae* | 73 08 012 |
| 2 | *Edwarsiella tarda* | 75 07 053 |
| 3 | *Citrobacter koseri* | 75 08 021 |
| 4 | *Shigella* spp | 76 02 055 |
| 5 | *E. coli* | 77 05 035 |
| 6 | *E. coli* | 78 12 004 |
| 7 | *Pectobacterium atrosepticum* | 80 12 075 |
| 8 | *Salmonella* ser. *Typhimurium* | 81 12 010 |
| 9 | *Pectobacterium carotovorum* | 84 06 059 |
| 10 | *Kluyvera ascorbata* | 84 08 084 |
| 11 | *Escherichia vulneris* | 85 06 777 |
| 12 | *Providencia rettgeri* | 88 05 064 |
| 13 | *Shigella flexneri* | 92 11 059 |
| 14 | *Shigella sonnei* | 92 11 060 |
| 15 | *Yersinia enterocolitica* ssp *enterocolitica* | 92 11 061 |
| 16 | *Providencia stuartii* | 92 12 101 |
| 17 | *Salmonella* spp | 93 03 001 |
| 18 | *Salmonella* ser. *Enteritidis* | 94 06 001 |
| 19 | *Leclercia adecarboxylata* | 97 04 041 |
| 20 | *Morganella morganii* ssp *morganii* | 97 08 046 |
| 21 | *Shigella boydii* | 00 04 212 |
| 22 | *Escherichia hermannii* | 04 03 161 |
| 23 | *Proteus mirabilis* | 04 05 048 |
| 24 | *Pantoea agglomerans* | 04 05 057 |
| 25 | *Proteus vulgaris* | 04 05 062 |
| 26 | *Enterobacter sakazakii* | 05 01 020 |
| 27 | *Rahnella aquatilis* | 05 04 103 |
| 28 | *Serratia liquefaciens* | 05 04 117 |
| 29 | *Cedecea lapagei* | 05 04 130 |
| 30 | *Raoultella ornithinolytica* | 05 04 140 |
| 31 | *Yersinia enterocolitica* | 05 04 143 |
| 32 | *E. coli* | 05 04 163 |
| 33 | *Citrobacter freundii* | 05 04 165 |

-continued

| | Species | API No. |
|---|---|---|
| 34 | Buttiauxella agrestis | 05 04 166 |
| 35 | Klebsiella oxytoca | 05 04 175 |
| 36 | Hafnia alvei | 05 04 201 |
| 37 | Enterobacter intermedius | 05 04 110 |
| 38 | E. coli | 05 06 043 |
| 39 | Ewingella americana | 05 06 045 |
| 40 | Enterobacter amnigenus | 05 06 046 |
| 41 | E. coli | 05 06 052 |
| 42 | Citrobacter braakii | 05 06 109 |
| 43 | Enterobacter cloacae | 05 09 064 |
| 44 | Pseudomonas aeruginosa | 89 09 041 | d) Reading of the Results

The results obtained are given in the table hereinafter:

| | | 4-(4'-aminostyryl)quinoline | | |
|---|---|---|---|---|
| Strain No. | C Growth | Growth | Coloration strength | Color |
| 1 | ++ | ++ | ++ | Orange |
| 2 | ++ | ++ | ++ | Orange |
| 3 | ++ | ++ | ++ | Orange |
| 4 | ++ | ++ | ++ | Orange |
| 5 | ++ | ++ | ++ | Orange |
| 6 | ++ | ++ | ++ | Orange |
| 7 | − | − | − | — |
| 8 | ++ | ++ | ++ | Orange |
| 9 | ++ | + | ++ | Orange |
| 10 | ++ | ++ | ++ | Orange |
| 11 | ++ | ++ | ++ | Orange |
| 12 | ++ | ++ | ++ | Orange |
| 13 | ++ | ++ | ++ | Orange |
| 14 | ++ | ++ | ++ | Orange |
| 15 | ++ | ++ | ++ | Orange |
| 16 | ++ | ++ | ++ | Orange |
| 17 | ++ | ++ | ++ | Orange |
| 18 | ++ | ++ | ++ | Orange |
| 19 | ++ | ++ | ++ | Orange |
| 20 | ++ | ++ | ++ | Orange |
| 21 | ++ | ++ | ++ | Orange |
| 22 | ++ | ++ | ++ | Orange |
| 23 | ++ | ++ | ++ | Orange |
| 24 | ++ | ++ | ++ | Orange |
| 25 | ++ | ++ | ++ | Orange |
| 26 | ++ | ++ | − | — |
| 27 | ++ | ++ | ++ | Orange |
| 28 | ++ | ++ | ++ | Orange |
| 29 | ++ | ++ | ++ | Orange |
| 30 | ++ | ++ | ++ | Orange |
| 31 | ++ | + | ++ | Orange |
| 32 | ++ | ++ | ++ | Orange |
| 33 | ++ | ++ | ++ | Orange |
| 34 | ++ | ++ | ++ | Orange |
| 35 | ++ | ++ | ++ | Orange |
| 36 | ++ | ++ | ++ | Orange |
| 37 | ++ | + | ++ | Orange |
| 38 | ++ | ++ | ++ | Orange |
| 39 | ++ | ++ | ++ | Orange |
| 40 | ++ | ++ | ++ | Orange |
| 41 | ++ | ++ | ++ | Orange |
| 42 | ++ | ++ | ++ | Orange |
| 43 | ++ | ++ | ++ | Orange |
| 44 | ++ | + | − | — | e) Conclusion 4-(4'-Aminostyryl)quinoline does not exhibit any particular toxicity.

Its use makes it possible to reveal an acidification via the appearance of a bright orange coloration which diffuses only a little after incubation for 24 h.

Under the conditions tested, the use of 4-(4'-aminostyryl)quinoline makes it possible to detect strains capable of fermenting glucose.

EXAMPLE 7

Use of Substrates of Formula I According to the Invention for Detecting a Variation in pH a) pH Indicators The 4-(4'-aminostyryl)quinoline compound was synthesized as described in example 1.

b) Preparation of the Medium

A stock solution containing 50 g/l of 4-(4'-aminostyryl)quinoline and a stock solution containing 40 g/l of Blue-b-D-GUR (i.e. 5-bromo-3-indoxyl-b-D-glucuronic acid) were prepared in a solvent of DMSO type and added to a modified chromID Coli® medium previously autoclaved and kept molten, in a proportion of 50 mg/l and 200 mg/l respectively. After homogenization, this medium was distributed into 120-mm-squared Petri dishes. A medium acting as a growth control (modified chromID Coli®) and denoted C was also poured.

*Composition of the modified chromID Coli® medium (in g/l):
Peptones: 5.5
Yeast extract: 8
Sodium chloride: 5
Bile salts: 0.7
Glucose: 10
Activator: 0.2
Agar: 12.5 c) Inoculation and Incubation

Forty-three strains of microorganisms (details in the table below) were inoculated in test spots: depositing of 1 µl using bacterial suspensions at 0.5 McFarland ($15 \times 10^4$ CFU/spot).

The media were incubated for 48 hours at 37° C., and then the spots formed were examined visually.

| | Species | API No. |
|---|---|---|
| 1 | Klebsiella pneumoniae ssp pneumoniae | 73 08 012 |
| 2 | Edwarsiella tarda | 75 07 053 |
| 3 | Citrobacter koseri | 75 08 021 |
| 4 | Shigella spp | 76 02 055 |
| 5 | E. coli | 77 05 035 |
| 6 | E. coli | 78 12 004 |
| 7 | Pectobacterium atrosepticum | 80 12 075 |
| 8 | Salmonella ser. Typhimurium | 81 12 010 |
| 9 | Pectobacterium carotovorum | 84 06 059 |
| 10 | Kluyvera ascorbata | 84 08 084 |
| 11 | Escherichia vulneris | 85 06 777 |
| 12 | Providencia rettgeri | 88 05 064 |
| 13 | Shigella flexneri | 92 11 059 |
| 14 | Shigella sonnei | 92 11 060 |
| 15 | Yersinia enterocolitica ssp enterocolitica | 92 11 061 |
| 16 | Providencia stuartii | 92 12 101 |
| 17 | Salmonella spp | 93 03 001 |
| 18 | Salmonella ser. Enteritidis | 94 06 001 |
| 19 | Leclercia adecarboxylata | 97 04 041 |
| 20 | Morganella morganii ssp morganii | 97 08 046 |
| 21 | Shigella boydii | 00 04 212 |
| 22 | Escherichia hermannii | 04 03 161 |
| 23 | Pantoea agglomerans | 04 05 057 |
| 24 | Proteus vulgaris | 04 05 062 |
| 25 | Enterobacter sakazakii | 05 01 020 |
| 26 | Rahnella aquatilis | 05 04 103 |
| 27 | Serratia liquefaciens | 05 04 117 |
| 28 | Cedecea lapagei | 05 04 130 |
| 29 | Raoultella ornithinolytica | 05 04 140 |

-continued

| Strain No. | Species | API No. |
|---|---|---|
| 30 | Yersinia enterocolitica | 05 04 143 |
| 31 | E. coli | 05 04 163 |
| 32 | Citrobacter freundii | 05 04 165 |
| 33 | Buttiauxella agrestis | 05 04 166 |
| 34 | Klebsiella oxytoca | 05 04 175 |
| 35 | Hafnia alvei | 05 04 201 |
| 36 | Enterobacter intermedius | 05 04 110 |
| 37 | E. coli | 05 06 043 |
| 38 | Ewingella americana | 05 06 045 |
| 39 | Enterobacter amnigenus | 05 06 046 |
| 40 | E. coli | 05 06 052 |
| 41 | Citrobacter braakii | 05 06 109 |
| 42 | Enterobacter cloacae | 05 09 064 |
| 43 | Acinetobacter lwoffi | 05 04 082 | d) Reading of the Results

The results obtained are given in the table hereinafter.

| Strain No. | C Growth | 4-(4'-aminostyryl)quinoline + Blue-b-GUR | | |
|---|---|---|---|---|
| | | Growth | Coloration strength | Color |
| 1 | ++ | ++ | ++ | orange |
| 2 | ++ | ++ | ++ | orange |
| 3 | ++ | ++ | ++ | orange |
| 4 | ++ | ++ | ++ | orangey-brown |
| 5 | ++ | ++ | ++ | brown |
| 6 | ++ | ++ | ++ | brown |
| 7 | − | − | − | — |
| 8 | ++ | ++ | ++ | orange |
| 9 | ++ | + | ++ | orange |
| 10 | ++ | ++ | ++ | orange |
| 11 | ++ | ++ | ++ | orange |
| 12 | ++ | ++ | ++ | orange |
| 13 | ++ | ++ | ++ | orange |
| 14 | ++ | ++ | ++ | orangey-brown |
| 15 | ++ | + | ++ | orange |
| 16 | ++ | ++ | ++ | orange |
| 17 | ++ | ++ | ++ | orange |
| 18 | ++ | ++ | ++ | orange |
| 19 | ++ | ++ | ++ | orange |
| 20 | ++ | ++ | ++ | orange |
| 21 | ++ | ++ | ++ | brown |
| 22 | ++ | ++ | ++ | orange |
| 23 | ++ | ++ | ++ | orange |
| 24 | ++ | ++ | ++ | orange |
| 25 | ++ | ++ | − | — |
| 26 | ++ | ++ | ++ | orange |
| 27 | ++ | ++ | + | orange |
| 28 | ++ | ++ | ++ | orange |
| 29 | ++ | ++ | ++ | orange |
| 30 | ++ | ++ | ++ | orange |
| 31 | ++ | ++ | ++ | brown |
| 32 | ++ | ++ | ++ | orange |
| 33 | ++ | ++ | ++ | orange |
| 34 | ++ | ++ | ++ | orange |
| 35 | ++ | ++ | ++ | orange |
| 36 | ++ | ++ | ++ | orange |
| 37 | ++ | + | ++ | brown |
| 38 | ++ | ++ | ++ | orange |
| 39 | ++ | ++ | ++ | orange |
| 40 | ++ | ++ | ++ | brown |
| 41 | ++ | ++ | ++ | orange |
| 42 | ++ | ++ | ++ | orange |
| 43 | ++ | ++ | ++ | orange |
| 44 | ++ | + | − | — | e) Conclusion 4-(4'-Aminostyryl)quinoline combined with Blue-b-GUR make it possible to simultaneously detect enterobacteria (acidification of glucose revealed by the orange coloration of 4-(4'-aminostyryl)quinolinium) and beta-glucuronidase-positive E. coli strains (and also Shigella—from a genomic point of view, Shigella strains belong to the E. coli. species) by the brown coloration of the colonies, a mixture of orange and blue (following hydrolysis of the Blue-b-GUR).

The invention claimed is:

1. A method for the detection in microorganisms of a peptidase activity comprising the following steps:
    a) providing a detecting and/or identifying medium comprising a compound of the following formula (I):

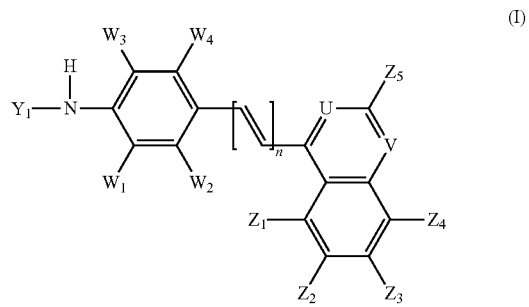

wherein:
   $Y_1$ is a peptide, H or an alkyl;
   $W_1, W_2, W_3$ and $W_4$ are independently H, Br, Cl, F, I, alkyl, alkoxy, thiomethyl, perfluoroalkyl, nitro, cyano, carboxyl, carboxyl esters or carboxyl amides or any combination thereof;
   n=0, 1 or 2;
   wherein if V is N or $N^+R$ then U is $CZ_6$;
   R is H, alkyl, aralkyl, aryl, alkanoyl or alkylsulfonyl;
   $Z_1, Z_2, Z_3, Z_4$ and $Z_5$ are independently H, Br, Cl, F, I, alkyl, aryl, alkoxy, perfluoroalkyl, nitro, cyano, carboxyl, sulfonyl, including the carboxyl or sulfonyl esters or amides,
and salts thereof,
    b) inoculating the medium with a biological sample to be tested,
    c) leaving to incubate, and
    d) detecting the presence of at least one peptidase activity; wherein the compound is also an indicator of pH variation.

2. A method for differentiating bacteria in terms of whether they belong to Gram-positive bacteria or to Gram-negative bacteria, comprising the following steps:
    a) providing a detecting and/or identifying medium comprising a compound of the following formula (I):

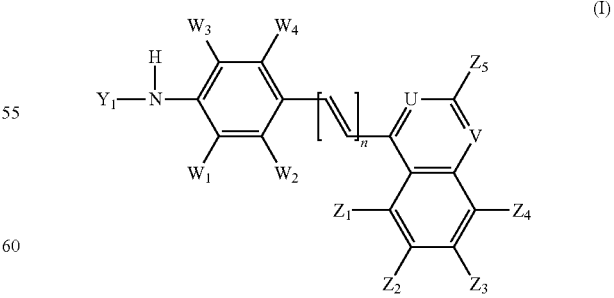

wherein:
   $Y_1$ is a peptide, H or an alkyl;
   $W_1, W_2, W_3$ and $W_4$ are independently H, Br, Cl, F, I, alkyl, alkoxy, thiomethyl, perfluoroalkyl, nitro, cyano, carboxyl, carboxyl esters or carboxyl amides or any combination thereof;

n=0, 1 or 2;

wherein if V is N or $N^+R$ then U is $CZ_6$;

R is H, alkyl, aralkyl, aryl, alkanoyl or alkylsulfonyl;

$Z_1, Z_2, Z_3, Z_4$ and $Z_5$ are independently H, Br, Cl, F, I, alkyl, aryl, alkoxy, perfluoroalkyl, nitro, cyano, carboxyl, sulfonyl, including the carboxyl or sulfonyl esters or amides, and salts thereof, b) inoculating the medium with a biological sample to be tested, c) leaving to incubate, and d) revealing the presence of at least one peptidase activity.

3. The method of claim 1, wherein $Y_1$ is a peptide.

4. The method of claim 1, wherein n=1.

5. The method of claim 1, wherein $W_1, W_2, W_3$ and $W_4$ are independently H.

6. The method of claim 1, wherein U is CH and V is N or $N^+R$.

7. The method of claim 1, wherein $Z_1, Z_2, Z_3$ and $Z_4$ are independently H.

8. The method of claim 1, wherein said compound is chosen from: L-alanyl-4-(4'-amidophenyl)-2-methylquinoline, L-alanyl-4-(4'-amidostyryl)-N-benzylquinolinium TFA, L-glutamyl-4-(4'-amidostyryl)-N-benzylquinolinium TFA, beta-alanyl-4-(4'-amidostyryl)-N-benzylquinolinium TFA, L-alanyl-4-(4'-amidostyryl)-N-methylquinolinium TFA, D-alanine-N-methyl-4-(4'-aminostyryl)quinolinium (dichloride), L-alanyl-2-(4'-amidostyryl)-N-methylquinolinium, Z-alanyl-2-(4'-amidostyryl)-N-methylquinolinium, L-alanyl-4-(4'-amidostyryl)-N-methylquinolinium (dichloride), L-alanyl-L-alanyl-4-(4'-amidostyryl)-N-methylquinolinium (dichloride), L-alanyl-L-alanyl-L-alanyl-4-(4'-amidostyryl)-N-methylquinolinium (dichloride), γ-aminobutyryl-4-(4'-amidostyryl)-N-methylquinolinium di-Cl, L-asparaginyl-4-(4'-amidostyryl)-N-methylquinolinium-bis-TFA, α-aspartyl-4-(4'-amidostyryl)-N-methylquinolinium dichloride, β-aspartyl-4-(4'-amidostyryl)-N-methylquinolinium dichloride, glycyl-4-(4'-amidostyryl)-N-methylquinolinium (dichloride), L-gamma-glutamyl-4-(4'-amidostyryl)-N-methylquinolinium (dichloride), glycyl-4-(4'-amidostyryl)-N-methylquinolinium chloride, L-leucyl-4-(4'-amidostyryl)-N-methylquinolinium dihydrochloride, L-methionyl-4-(4'-amidostyryl)-N-methylquinolinium di-Cl, pyroglutamyl-4-(4'-amidostyryl)-N-methylquinolinium iodide, L-tryptophanyl-4-(4-amidostyryl)-N-methylquinolinium dihydrochloride, L-tyrosyl-4-(4'-amidostyryl)-N-methylquinolinium dihydrochloride, beta-alanyl-2-(4'-amidostyryl)-N-methylquinolinium TFA, L-prolyl-2-(4'-amidostyryl)-N-methylquinolinium (HBr), Z-arginyl-2-(4'-amidostyryl)-N-methylquinolinium, L-pyroglutamyl-2-(4'-amidostyryl)-N-methylquinolinium, L-alanyl-4-(4'-amidostyryl)quinoline TFA, β-alanyl-4-(4'-amidostyryl)quinoline, L-glutamyl-4-(4'-amidostyryl)quinoline TFA, glycyl-4-(4'-amidostyryl)quinoline TFA, pyroglutamyl-4-(4'-amido styryl)quinoline, L-alanyl-2-(4'-amidostyryl)quinoline, β-alanyl-2-(4'-amidostyryl)quinoline, glycyl-2-(4'-amidostyryl)quinoline TFA and L-alanyl-2-(2'-pyridyl)-4-(4''-amidostyryl)quinoline.

* * * * *